United States Patent
Park et al.

(10) Patent No.: US 11,207,019 B1
(45) Date of Patent: Dec. 28, 2021

(54) APPARATUS AND METHOD FOR PROVIDING INFORMATION ON PARKINSON'S DISEASE USING NEUROMELANIN IMAGE

(71) Applicant: Heuron Co., Ltd., Incheon (KR)

(72) Inventors: Seongbeom Park, Incheon (KR); Soo Hwa Song, Uijeongbu-si (KR)

(73) Assignee: Heuron Co., Ltd., Incheon (KR)

( * ) Notice: Subject to any disclaimer, the term of this patent is extended or adjusted under 35 U.S.C. 154(b) by 0 days.

(21) Appl. No.: 17/220,985

(22) Filed: Apr. 2, 2021

(30) Foreign Application Priority Data

Feb. 5, 2021 (KR) ........................ 10-2021-0016667

(51) Int. Cl.
*G06K 9/00* (2006.01)
*A61B 5/00* (2006.01)
(Continued)

(52) U.S. Cl.
CPC .......... *A61B 5/4082* (2013.01); *A61B 5/0042* (2013.01); *A61B 5/055* (2013.01);
(Continued)

(58) Field of Classification Search
CPC ......... G06T 7/0012; G06T 2207/30048; G06T 2207/10088; G06T 7/0014; G06T 2207/10072; G06T 2207/30016; G06T 2207/10081; G06T 7/73; G06T 2200/04; G06T 11/60; G06T 2207/10104; G06T 2207/10108; G06T 2210/41; G06T 7/62;
(Continued)

(56) References Cited

U.S. PATENT DOCUMENTS

| | | | | |
|---|---|---|---|---|
| 11,013,452 B1 * | 5/2021 | Song | ................. | G06K 9/6267 |
| 2008/0123922 A1 * | 5/2008 | Gielen | ................. | A61B 6/5241 |
| | | | | 382/131 |
| 2015/0125057 A1 | 5/2015 | Huddleston et al. | | |

FOREIGN PATENT DOCUMENTS

| | | |
|---|---|---|
| CN | 111681184 A | 9/2020 |
| KR | 10-1540254 B1 | 7/2015 |

(Continued)

OTHER PUBLICATIONS

Ariz "Dynamic Atlas-Based Segmentation and Quantification of Neuromelanin-Rich Brainstem Structures in Parkinson Disease", Mar. 2019, IEEE Transaction on Medical Imaging (Year: 2019).*
(Continued)

*Primary Examiner* — Alex Kok S Liew
(74) *Attorney, Agent, or Firm* — Sughrue Mion, PLLC

(57) ABSTRACT

The Parkinson's disease information providing apparatus using a neuromelanin image according to an aspect of the present disclosure includes an image receiving unit which acquires an MRI image obtained by capturing a brain of a patient; an image preprocessing unit which preprocesses the acquired MRI image to observe the neuromelanin region used as an image bio marker of the Parkinson's disease; an image processing unit which analyzes the preprocessed MRI image to classify a first image including the neuromelanin region and detects the neuromelanin region from the classified first image; and an image analyzing unit which diagnoses whether the patient has the Parkinson's disease by analyzing whether the detected the neuromelanin region is normal.

21 Claims, 17 Drawing Sheets

(51) Int. Cl.
*G06K 9/42* (2006.01)
*G06K 9/62* (2006.01)
*G06T 3/40* (2006.01)
*G06T 7/11* (2017.01)
*G06T 7/174* (2017.01)
*G06T 7/194* (2017.01)
*A61B 5/055* (2006.01)

(52) U.S. Cl.
CPC .......... *A61B 5/7246* (2013.01); *A61B 5/7267* (2013.01); *G06K 9/42* (2013.01); *G06K 9/6267* (2013.01); *G06T 3/40* (2013.01); *G06T 7/11* (2017.01); *G06T 7/174* (2017.01); *G06T 7/194* (2017.01); *G06T 2207/10096* (2013.01); *G06T 2207/20081* (2013.01); *G06T 2207/20084* (2013.01); *G06T 2207/20128* (2013.01); *G06T 2207/20132* (2013.01); *G06T 2207/30016* (2013.01)

(58) Field of Classification Search
CPC .......... G06T 11/008; G06T 7/11; G06T 7/149; G06T 11/00; G06T 11/001; G06T 15/10; G16H 30/20; G16H 30/40; G16H 50/50; G16H 50/70; G16H 50/30; G16H 10/40; G16H 10/60; G16H 70/00; G16H 50/20; G16H 15/00
See application file for complete search history.

(56) References Cited

FOREIGN PATENT DOCUMENTS

| | | |
|---|---|---|
| KR | 10-2016-0058812 A | 5/2016 |
| KR | 10-1754291 B1 | 7/2017 |
| KR | 10-1860566 B1 | 5/2018 |
| KR | 10-2018-0106739 A | 10/2018 |
| KR | 10-2058884 B1 | 12/2019 |
| KR | 10-2068836 B1 | 2/2020 |
| WO | 2020/077098 A1 | 4/2020 |

OTHER PUBLICATIONS

Korean Patent Office, Notice of Preliminary Rejection dated Apr. 8, 2021 in copending Applcaition No. 10-2021-0016667 with English translation.

Korean Patent Office, Decision for Grant of Patent dated May 14, 2021 in copending Application No. 10-2021-0016667 with English translation.

Shinde et al., "Predictive markers for Parkinson's disease using deep neural nets on neuromelanin sensitive MRI", NeuroImage: Clinical 22, Mar. 2019, 101748.

Se Jin Cho et al., "Diagnostic performance of neuromelanin-sensitive magnetic resonance imaging for patients with Parkinson's disease and factor analysis for its heterogeneity: a systematic review and meta-analysis", European Radiology, 2021, vol. 31, pp. 1268-1280 (13 pages total).

* cited by examiner (a)  (b)

(a)

(c)

NM-MRI template
(b)

150

(a) (b)

(a)          (b)

160

(a)

(b)

(c)

(d)

200

Baseline data
(a)

f/u data
(b)

Within-subject template
(c)

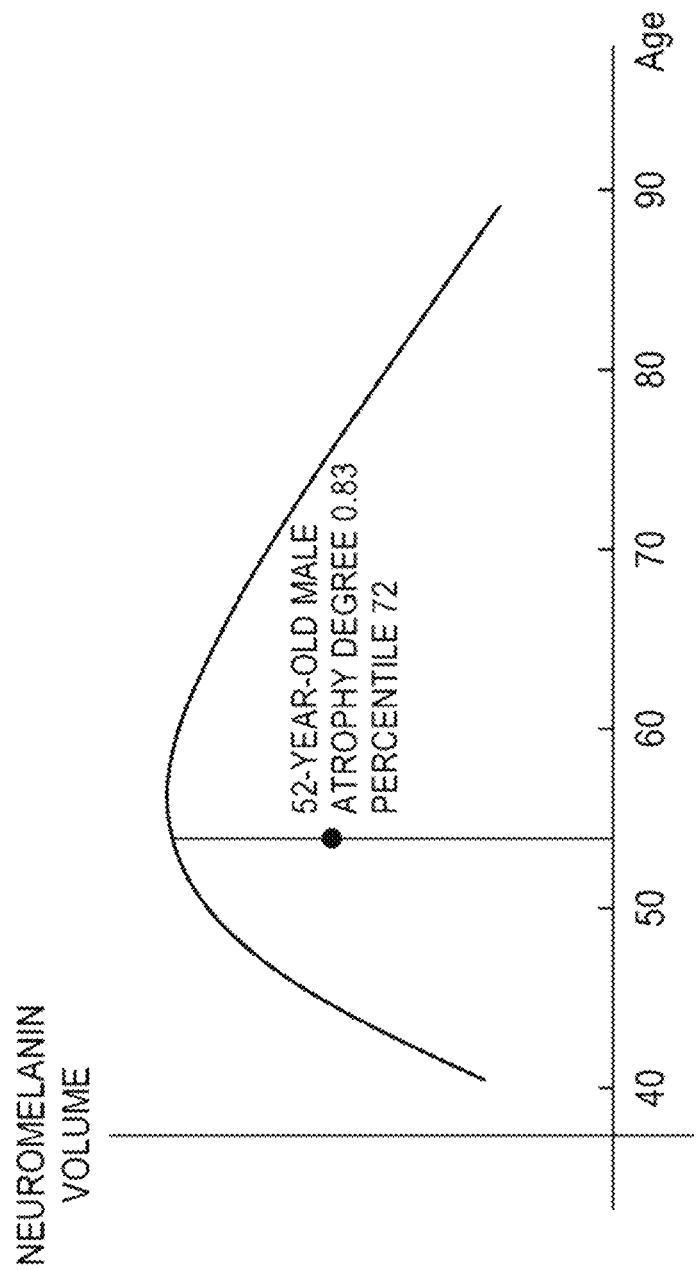

APPARATUS AND METHOD FOR PROVIDING INFORMATION ON PARKINSON'S DISEASE USING NEUROMELANIN IMAGE

CROSS-REFERENCE TO RELATED APPLICATIONS

This application claims the priority of Korean Patent Application No. 10-2021-0016667 filed on Feb. 5, 2021, in the Korean Intellectual Property Office, the disclosure of which is incorporated herein by reference.

BACKGROUND

Field

The present disclosure relates to an apparatus and a method for providing information on Parkinson's disease using a neuromelanin image, and more particularly, to an apparatus and a method for providing customized information related to Parkinson's disease by analyzing neuromelanin related magnetic resonance imaging (hereinafter, abbreviated as "MRI") based on artificial intelligence (AI).

Description of the Related Art

The neurodegenerative disorder refers to a disease which causes an abnormal brain function as nerve cells die due to some reasons.

Representative neurodegenerative disorders usually include Alzheimer's disease, Parkinson's disease, and rarely, Lou Gehrig's disease.

Among the neurodegenerative disorders, the Parkinson's disease is a representative neurodegenerative disorder by which neural cells are destroyed and is accompanied by depression and anxiety together with symptoms such as rigidity, hand and foot tremors, and difficulty in walking so that the quality of life is greatly degraded.

The neurodegenerative disorder is diagnosed by a non-invasive method of diagnosing without contact with mucosa, skin break, and internal body cavity beyond a natural or artificial body orifice.

RELATED ART DOCUMENT

Patent Document

1. Korean Registered Patent No. 10-1754291 (published on Jul. 6, 2017)
2. Korean Unexamined Patent Application Publication No. 10-2016-0058812 (published on May 25, 2016)

SUMMARY

Until now, [18F]FP-CIT Positron emission tomography (PET) using isotopes has been used as the most objective method for a diagnosis of Parkinson's disease and a differential diagnosis of drug-induced Parkinsonism.

However, [18F]FP-CIT PET is a very expensive test method and has a risk of radiation exposure.

Therefore, it is requested to develop a technology for early diagnosis of the Parkinson's disease by observing a neuromelanin region using the MRI.

An object of the present disclosure is to solve the problems as described above and to provide an apparatus and a method for helping diagnose Parkinson's disease early by predicting a risk of the Parkinson's disease according to ages by analyzing the MRI.

Another object of the present disclosure is to provide an apparatus and a method for outputting customized information related to the Parkinson's disease by analyzing a neuromelanin image proposed as an image bio marker of the Parkinson's disease.

Further, an object of the present disclosure is to provide an apparatus and a method which preprocess an acquired MRI image to observe a neuromelanin image, analyze the preprocessed MRI image to classify an image including the neuromelanin image, detect a neuromelanin image from the classified image, and predict the risk of the Parkinson's disease according to the age of the patient by means of the detected neuromelanin and clinical information.

Further, an object of the present disclosure is to provide an apparatus and a method which perform at least one operation of angle adjustment, image enlargement, and reslice based on an image from which a skull region is removed, detect a region including neuromelanin using a deep neural network model, perform spatial normalization using a template image, and generate a CR image in which a contrast ratio (CR) value is mapped to each voxel of the image to predict a risk of the Parkinson's disease.

Further, an object of the present disclosure is to provide an apparatus and a method which segment a predetermined vulnerable region based on a generated CR image and calculate a mean CR in the segmented vulnerable region to perform preprocessing on the image.

Further, an object of the present disclosure is to provide an apparatus and a method which provide a longitudinal study function by generating a within-subject template and performing spatial normalization using neuromelanin region data included in a plurality of MRI images when there is a plurality of MRI images input with respect to the same subject (when a plurality of MRI images captured from the same person at different timings is analyzed).

Further, an object of the present disclosure is to provide an apparatus and a method which calculate a volume of a neuromelanin region of a patient, calculate a neuromelanin atrophy degree using the calculated volume of the neuromelanin region and the acquired clinical information together, and predict the risk of the Parkinson's disease of the patient based on the calculated neuromelanin atrophy degree.

Further, an object of the present disclosure is to provide an apparatus and a method which calculate a neuromelanin atrophy rate of a patient using a plurality of neuromelanin atrophy degrees acquired from the same person at different timings and display and provide the neuromelanin atrophy rate of the patient in various forms.

Further, an object of the present disclosure is to provide a device, a system, and a method which increase a probability of successful clinical trials by predicting a risk of the Parkinson's disease using artificial intelligence.

In the meantime, technical objects to be achieved in the present disclosure are not limited to the aforementioned technical objects, and another not-mentioned technical object will be obviously understood by those skilled in the art from the description below.

According to an aspect of the present disclosure to achieve the technical object, a Parkinson's disease risk predicting apparatus using a neuromelanin image includes an image receiving unit which acquires an MRI image obtained by capturing a brain of a patient; an image preprocessing unit which preprocesses the acquired MRI image to observe the neuromelanin region used as an image bio marker of the Parkinson's disease; an image processing unit which analyzes the preprocessed MRI image to classify a first image including the neuromelanin region and detects the neuromelanin region from the classified first image; and an image analyzing unit which standardizes the detected neuromelanin region volume together with clinical information to predict a risk of the Parkinson's disease according to the age of the patient.

Further, the image preprocessing unit may generate a contrast ratio (CR) image based on the acquired MRI image.

Further, the image preprocessing unit may include: a skull removing unit which removes a skull region from the acquired MRI image; an image reslicing unit which performs at least one operation of angle adjustment, image enlargement, and reslice, based on the image in which the skull region is removed; a neuromelanin region classifying unit which detects a first region including the neuromelanin using a deep neural network model, based on the image transmitted from the image reslicing unit; a spatial normalizing unit which performs the spatial normalization using a template image based on an image in which the first region is detected; a CR image generating unit which generates a CR image in which the contrast ratio (CR) value is mapped to each voxel of the image based on the spatially normalized image; and a calculating unit which segments a predetermined vulnerable region and calculates a mean CR in the segmented vulnerable region, based on the generated CR image.

Further, the neuromelanin region classifying unit displays a boundary of the first region to be identified and may crop an image of the first region.

Further, the spatial normalizing unit may perform the spatial normalization using at least one of a first template image generated from a neuromelanin MRI image of a normal person and a second template image generated from the anatomical image based on a T1-weighted MRI.

Further, the apparatus further includes a reference region segmentation unit which segments a reference region using an Atlas-based segmentation method, based on the spatially normalized image and calculates a mean value in the segmented reference region and the CR image generating unit may calculate the contrast ratio value using the calculated mean value.

Further, the contrast ratio value may be calculated by the following Equation 1.

$$CR_v = \frac{(SI_v - \text{mean}SI_{Ref})}{\text{mean}SI_{Ref}} \quad \text{[Equation 1]}$$

In Equation 1, $CR_v$ is the contrast ratio value, $SI_v$ is a signal intensity of each voxel, and $\text{mean}SI_{Ref}$ refers to the mean value.

Further, the segmented reference region may be a cerebral peduncles region.

Further, the predetermined vulnerable region may be a region which significantly differs by more than a predetermined reference when a neuromelanin region of the normal group and a neuromelanin region of a patient group are compared.

Further, the predetermined vulnerable region may include nigrosome1 region and nigrosome2 region.

when a plurality of MRI images is input with respect to the same subject (a plurality of MRI images captured from the same person at different timings), the apparatus may further include a template generating unit which generates a within-subject template using the neuromelanin region data included in the plurality of MRI images and the spatial normalizing unit performs the spatial normalization using the within-subject template and the within-subject template may be used for a longitudinal study for the same subject.

Further, the image processing unit calculates a volume of the neuromelanin region based on the first image and the image analyzing unit may predict the risk of the Parkinson's disease of the patient using the calculated volume of the neuromelanin region and clinical information.

Further, the image processing unit may calculate the volume of the neuromelanin region using a number of voxels related to the first image and a voxel size.

Further, the image processing unit may classify the first image based on a graph-cut algorithm which uses a foreground image configured by voxels having a high probability of including a neuromelanin region and a background image generated based on the foreground image.

Further, the image processing unit may classify the first image based on a deep neural network trained with data in which a brain image and a neuromelanin region image are labeled.

Further, the image processing unit extracts a factor which is equal to or higher than a predetermined signal intensity and may classify the first image using the extracted factor.

Further, the image processing unit calculates a volume of the neuromelanin region based on the first image and further includes: a clinical information receiving unit which acquires clinical information, the image analyzing unit calculates a neuromelanin atrophy degree using the calculated volume of the neuromelanin region and the acquired clinical information together and may predict the risk of the Parkinson's disease of the patient according to the ages based on the calculated neuromelanin atrophy degree.

Further, the neuromelanin atrophy degree may be calculated by comparing a volume of the neuromelanin region extracted from an image of a normal group and a volume of the neuromelanin region of the patient.

Further, the image analyzing unit may convert the calculated neuromelanin atrophy degree into percentile information according to ages.

Further, the image analyzing unit calculates a neuromelanin atrophy rate of the patient using a plurality of neuromelanin atrophy degrees acquired for the same person captured at different timings and further includes a diagnostic information output unit which displays the neuromelanin atrophy rate of the patient.

In the meantime, according to another aspect of the present disclosure to achieve the technical object, in a system which increases a probability of successful clinical trials by screening a patient group having a high risk of the Parkinson's disease using a Parkinson's disease risk predicting apparatus including an image receiving unit, an image preprocessing unit, an image processing unit, and an image analyzing unit, and a central management unit, and/or a server which communicates with the Parkinson's disease information providing apparatus, the image receiving unit acquires MRI images obtained by capturing brains of a plurality of patients which is a clinical trial experimental candidate group for demonstration of drug efficacy, the image preprocessing unit preprocesses the acquired MRI image to observe the neuromelanin region used as an image bio marker of the Parkinson's disease, the image processing unit analyzes the preprocessed MRI image to classify a first image including the neuromelanin region and detects the neuromelanin region from the classified first image, the image analyzing unit analyzes whether the detected neuromelanin region is normal to transmits at least one information about a first patient which has the Parkinson's disease, among the plurality of patients to the central management unit and/or the server, and the central management unit and/or the server may use the clinical trial result for the first patient to demonstrate the drug efficacy.

As described above, according to the Parkinson's disease information providing apparatus and method according to the present disclosure, only images including the neuromelanin region are classified from the MRI and the neuromelanin region is analyzed from the classified image to predict the risk of the Parkinson's disease according to the age.

Further, according to the present disclosure, the Parkinson's disease is diagnosed using the image so that the Parkinson's disease is precisely diagnosed using the MRI equipment which is generally supplied, and the precision of the diagnosis result is improved.

Further, according to the present disclosure, only the neuromelanin region may be observed.

Specifically, the acquired MRI image is preprocessed to observe the neuromelanin image, the preprocessed MRI image is analyzed to classify an image including the neuromelanin image, the neuromelanin image is detected from the classified image, and whether the detected neuromelanin region is normal is analyzed to diagnose whether the patient has the Parkinson's disease.

Further, according to the present disclosure, the neuromelanin region may be effectively detected by machine learning.

Specifically, according to the present disclosure, the Parkinson's disease may be diagnosed by performing at least one operation of angle adjustment, image enlargement, and reslice based on an image from which a skull region is removed, detecting a region including neuromelanin using a deep neural network model, performing spatial normalization using a template image, and generating a CR image in which a contrast ratio (CR) value is mapped to each voxel of the image to diagnose the Parkinson's disease.

Further, according to the present disclosure, it is possible to provide an apparatus and a method which segment a predetermined vulnerable region based on a generated CR image and calculate a mean CR in the segmented vulnerable region to perform preprocessing on the image.

Further, according to the present disclosure, it is possible to provide a longitudinal study function by generating a within-subject template and performing spatial normalization using neuromelanin region data included in a plurality of MRI images when there is a plurality of MRI images input with respect to the same object.

Further, according to the present disclosure, it is possible to provide an apparatus and a method which calculate a volume of a neuromelanin region of a patient, calculate a neuromelanin atrophy degree using the calculated volume of the neuromelanin region and the acquired clinical information together, and diagnose whether the patient has the Parkinson's disease based on the calculated neuromelanin atrophy degree.

Further, according to the present disclosure, the neuromelanin atrophy rate of the patient is calculated using a plurality of neuromelanin atrophy degrees acquired at a predetermined period and the neuromelanin atrophy rate of the patient is displayed and provided in various forms.

In addition, according to the present disclosure, a result of clinical trials for demonstration of drug efficacy is determined by showing a statistical significance indicating whether to achieve a predicted expected effect for clinical trial participants. However, when the Parkinson's disease diagnosing method and apparatus according to the present disclosure are applied, only Parkinson's disease patients exactly targeted by new drugs are included as clinical trial subjects so that the probability of successful clinical trials may be increased as much as possible.

That is, the Parkinson's disease diagnosing method using artificial intelligence according to the present disclosure may be utilized to screen a patient group and a normal group to increase the probability of successful clinical trials.

A technical object to be achieved in the present disclosure is not limited to the aforementioned effects, and another not-mentioned effects will be obviously understood by those skilled in the art from the description below.

BRIEF DESCRIPTION OF DRAWINGS

The above and other aspects, features and other advantages of the present disclosure will be more clearly understood from the following detailed description taken in conjunction with the accompanying drawings, in which:

FIG. 16 illustrates an example of visibly displaying percentile information according to ages, by a diagnostic information output unit, according to the present disclosure.

DETAILED DESCRIPTION OF THE PREFERRED EMBODIMENT

Figure 1:
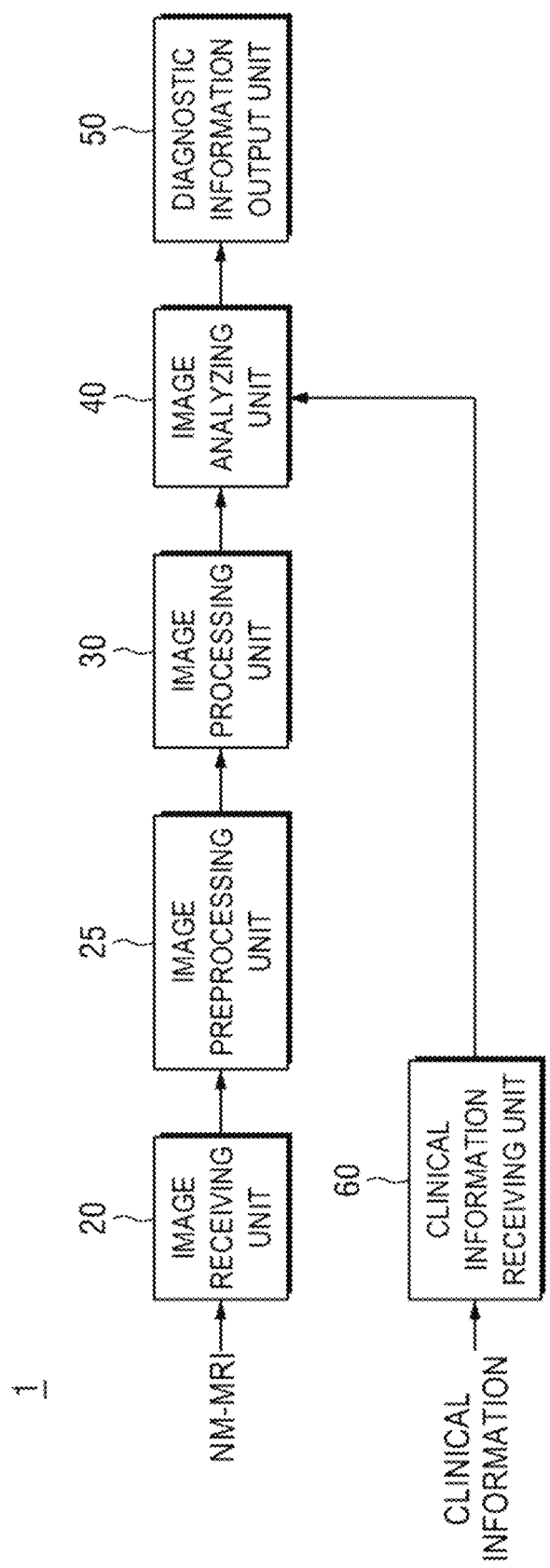
FIG. 1 illustrates a block diagram of a Parkinson's disease information providing apparatus according to the present disclosure.

Hereinafter, an exemplary embodiment of the present disclosure will be described with reference to the accompanying drawings. The exemplary embodiments which will be described below do not unduly limit the contents of the present disclosure as set forth in the claims and the entire configuration described in the present embodiment cannot be said to be essential as a solution for the present disclosure.

Hereinafter, a Parkinson's disease information providing apparatus and method according to an exemplary embodiment of the present disclosure will be described in detail with reference to the accompanying drawings.

In the meantime, the meaning "diagnosis" to be applied according to the present disclosure includes all the meanings of determining information related to the Parkinson's disease as well as the determining whether there is a Parkinson's disease.

For example, the meaning of "diagnosis" may include all determinations of brain atrophy degree prediction information according to ages, brain percentile information according to ages, and brain risk information related to the Parkinson's disease even though there is no Parkinson's disease.

Neuromelanin and Parkinson's Disease

Neuromelanin is an insoluble dark pigment composed of melanin, protein, lipid, and metal ions.

Neurons including neuromelanin are present in a specific brain area of a human central nervous system and a concentration is very high in dopaminergic neurons of substantia nigra (SN) and noradrenaline neurons of locus coeruleus (LC).

The neuromelanin is synthesized by iron-dependent oxidation of dopamine, norepinephrine, and catecholamine present in the cytoplasm.

When the neuromelanin is initially present in the cytoplasm, the neuromelanin is accumulated in organelles by macroautophagy, and the vacuoles are coupled to autophagic vacuoles including lysosomes and protein components to finally form organelles including neuromelanin.

Organelles containing neuromelanin first appear between two and three years old and are gradually accumulated with age. It is known that the neurons are increased to approximately 60 years old and then decreased.

It is known that the Parkinson's disease (PD) is caused by iron components which are deposited in the SN of the midbrain.

Irons cause the stress of brain tissues and death of the cells.

The neuromelanin in the SN plays a role in holding iron components introduced from the outside so that when irons are deposited more than a limit that the neuromelanin may accept, stress is caused in the tissues, which may lead to the Parkinson's disease.

The iron component may be non-invasively imaged by means of neuromelanin-sensitive MRI (NM-MRI) using the paramagnetic property of the neuromelanin and iron complexes.

The NM-MRI generates a hyperintensity signal of the neuromelanin complex.

The NM-MRI is verified by measuring a loss of the dopamine neuron of the SN and several studies have proved that the NM-MRI allows the loss of the neuron containing the neuromelanin from the SN of the Parkinson's disease patient to be observed.

As a result, when the degree of the neuromelanin is quantified in the NM-MRI, the Parkinson's disease may be diagnosed early to be prevented or a treatment schedule may be established.

However, the degree of the neuromelanin varies depending on the ages so that it is difficult to find out the individual's state.

Accordingly, there is a growing need for a device, a system, and a method which provide neuromelanin atrophy information according to the age by a machine learning model and enable prognosis prediction through the longitudinal study, by utilizing ages and various clinical information.

Parkinson's Disease Information Providing Apparatus Using Neuromelanin Image

FIG. 1 illustrates a block diagram of a Parkinson's disease information providing apparatus according to the present disclosure.

A Parkinson's disease information providing apparatus 1 according to an exemplary embodiment of the present disclosure includes an image receiving unit 20, an image preprocessing unit 25, an image processing unit 30, an image analyzing unit 40, and a diagnostic information output unit 50 as illustrated in FIG. 1.

First, the image receiving unit 20 may acquire MRI images obtained by capturing a brain of a patient.

The image receiving unit 20 may additionally acquire PET images related to the brain of the patient, as well as the MRI.

Next, the image preprocessing unit 25 provides a function of preprocessing the acquired MRI image to observe a neuromelanin region which is used as an image bio marker of the Parkinson's disease.

As the most important function of the image preprocessing unit 25, the image preprocessing unit 25 may generate a contrast ratio (CR) image based on the acquired MRI image.

Further, the image processing unit 30 provides a function of analyzing the preprocessed MRI image to classify a first image including the neuromelanin region and detecting the neuromelanin region from the classified first image.

The image processing unit 30 may calculate a volume of the neuromelanin region based on the first image and the image analyzing unit 40 may diagnose the Parkinson's disease of the patient based on the calculated volume of the neuromelanin region.

The image processing unit 30 may calculate the volume of the neuromelanin region using a number of voxels related to the first image and a voxel size.

Further, the image analyzing unit 40 may analyze whether the detected neuromelanin region is normal to diagnose whether the patient has the Parkinson's disease.

Further, the image analyzing unit 40 calculates a neuromelanin atrophy degree using the calculated volume of the neuromelanin region and the acquired clinical information together and may diagnose whether the patient has the Parkinson's disease based on the calculated neuromelanin atrophy degree.

Further, the image analyzing unit 40 may convert the calculated neuromelanin atrophy degree into percentile information according to ages.

When the image analyzing unit 40 calculates a neuromelanin atrophy rate of the patient using a plurality of neuromelanin atrophy degrees acquired at a predetermined period, the diagnostic information output unit 50 may provide a function of displaying the neuromelanin atrophy rate of the patient in various forms.

Hereinafter, roles and functions of components will be described in detail with reference to the drawings.

Configuration and Operation of Image Preprocessing Unit

Figure 2:
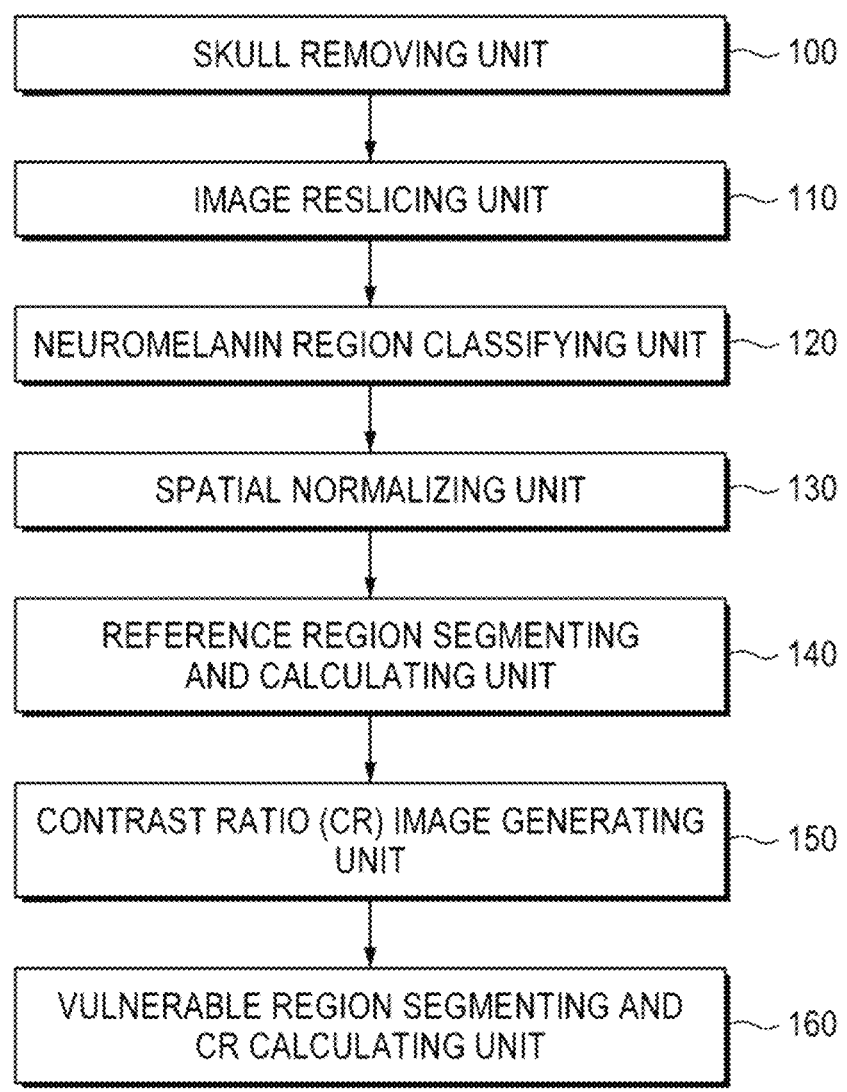
FIG. 2 illustrates an example of a block diagram of an image preprocessing unit according to the present disclosure.

FIG. 2 illustrates an example of a block diagram of an image preprocessing unit according to the present disclosure.

The image preprocessing unit 25 aims to generate a contrast ratio (CR) image based on the acquired MRI image.

Referring to FIG. 2, the image preprocessing unit 25 includes a skull removing unit 100, an image reslicing unit 110, a neuromelanin region classifying unit 120, a spatial normalizing unit 130, a reference region segmenting and calculating unit 140, a CR image generating unit 150, and a CR calculating unit 160.

First, the skull removing unit 100 provides a function of removing a skull region from the acquired MRI image.

Figure 3:
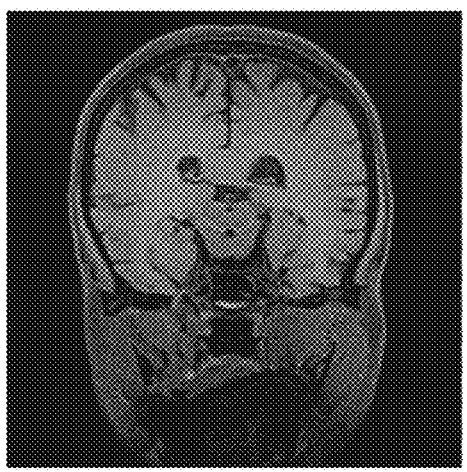
FIG. 3 illustrates an example of removing a non-brain tissue such as a skull from the neuromelanin MRI, according to the present disclosure.
Figure 3:
Figure 3:
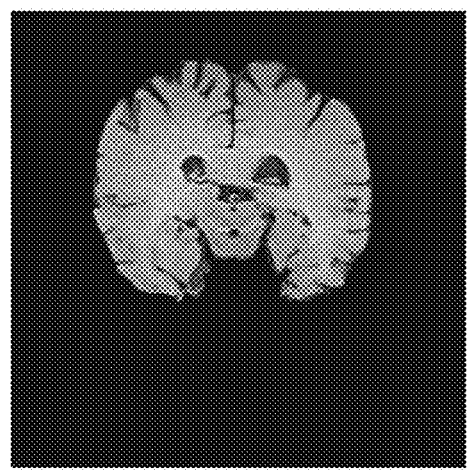

FIG. 3 illustrates an example of removing a non-brain tissue such as a skull from the neuromelanin MRI, according to the present disclosure.

FIG. 3 (a) illustrates an example of the input neuromelanin MRI (NM-MRI) image and FIG. 3 (b) illustrates an example in which a non-brain tissue is removed from the NM-MRI.

Next, the image reslicing unit 110 provides a function of performing at least one operation of angle adjustment, image enlargement, and reslice, based on the image in which the skull region is removed.

Figure 4:
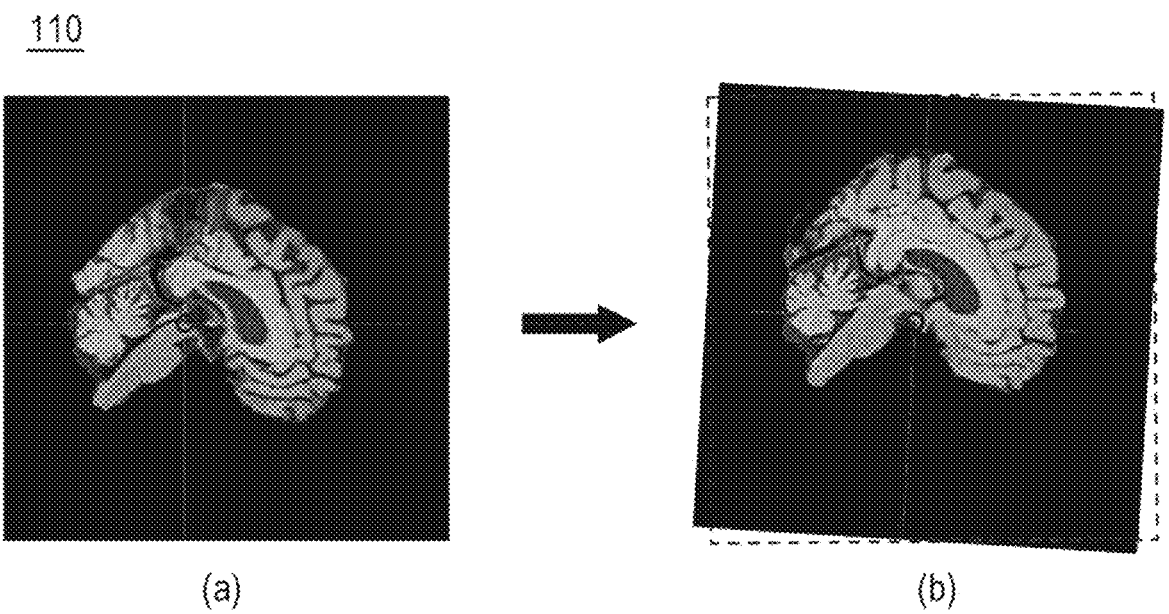
FIG. 4 illustrates an example of an operation of an image preprocessing unit which redistributes the image in a positive direction while maintaining spacing and direction cosines of the image to be constant, according to the present disclosure.

FIG. 4 illustrates an example of an operation of an image preprocessing unit which redistributes the image in a positive direction while maintaining spacing and direction cosines of the image to be constant, according to the present disclosure.

FIG. 4 (a) illustrates an example of an image before being resliced and FIG. 4 (b) illustrates an example of a result of redistributing the image in a positive direction while maintaining the spacing and direction cosines of the image to be constant.

Further, the neuromelanin region classifying unit 120 provides a function of detecting a first region including the neuromelanin using a deep neural network model, based on the image transmitted from the image reslicing unit.

At this time, the neuromelanin region classifying unit 120 may display the boundary of the first region to be identified and crop the image of the first image.

Figure 5:
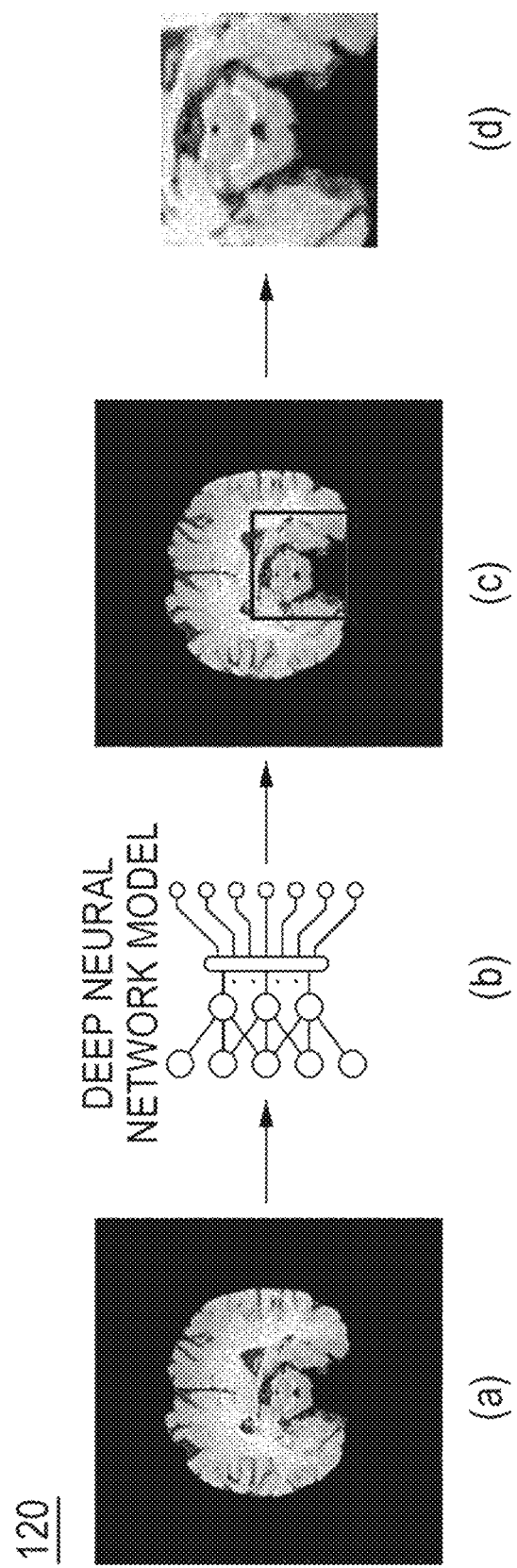
FIG. 5 illustrates an example of classifying a neuromelanin region, according to the present disclosure.

FIG. 5 illustrates an example of classifying a neuromelanin region, according to the present disclosure.

Referring to FIG. 5, the image transmitted from the image reslicing unit 110 is illustrated in FIG. 5 (a) and an example in which a region including the neuromelanin in the entire NM-MRI is detected by means of the deep neural network model illustrated in FIG. 5 (b) is illustrated in FIG. 5 (c).

Further, as illustrated in FIG. 5 (d), a boundary is displayed therearound and then the image may be cropped.

Further, the spatial normalizing unit 130 provides a function of performing the spatial normalization using a template image based on an image in which the first region is detected.

At this time, the spatial normalizing unit 130 performs the spatial normalization using at least one of a first template image generated from a neuromelanin MRI image of a normal person and a second template image generated from the anatomical image based on a T1-weighted MRI.

Further, the spatial normalizing unit 130 matches the first template image after matching using the second template image to perform the spatial normalization.

The spatial normalization refers to the spatial normalization of the input NM-MRI to the template image and according to the present disclosure, the spatial normalization uses any one of two methods.

According to the first method, the spatial normalization to the NM-MRI template is performed and the NM-MRI template refers to a template generated from NM-MRI of a plurality of normal people.

According to the second method, an anatomic image such as T1-weighted MRI is utilized.

Figure 6:
FIG. 6 illustrates an example of spatially normalizing the input neuromelanin MRI to a template image, according to the present disclosure.
Figure 6:
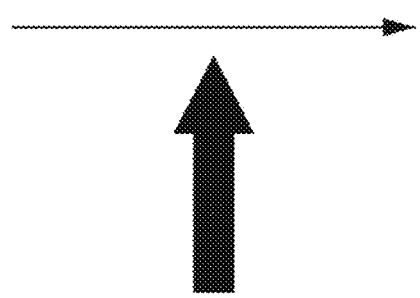
Figure 6:
Figure 6:
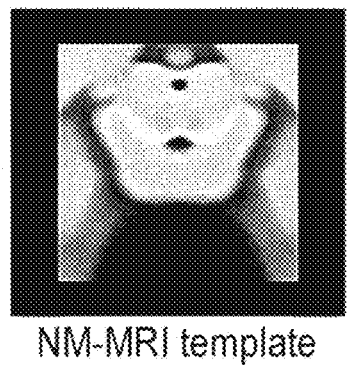

FIG. 6 illustrates an example of spatially normalizing the input neuromelanin MRI to a template image, according to the present disclosure.

As illustrated in FIGS. 6 (a) to (c), the above-described two methods may be combined so that after matching a high resolution T1-weighted MRI image of an individual to the T1 template, the NM-MRI of the individual is spatially normalized.

Further, the reference region segmenting and calculating unit 140 provides a function of segmenting the reference region using an Atlas-based segmentation method based on the spatially normalized image and calculating a mean value in the segmented reference region.

The segmented reference region may be a cerebral peduncles region.

That is, the reference region is segmented by the Atlas-based segmentation method to which a predefined atlas is applied and the mean in the reference region may be calculated in the NM-MRI.

In this process, a method using prior knowledge or a segmentation method using a reference image (atlas) defined in a template space by an expert may be utilized.

Figure 7:
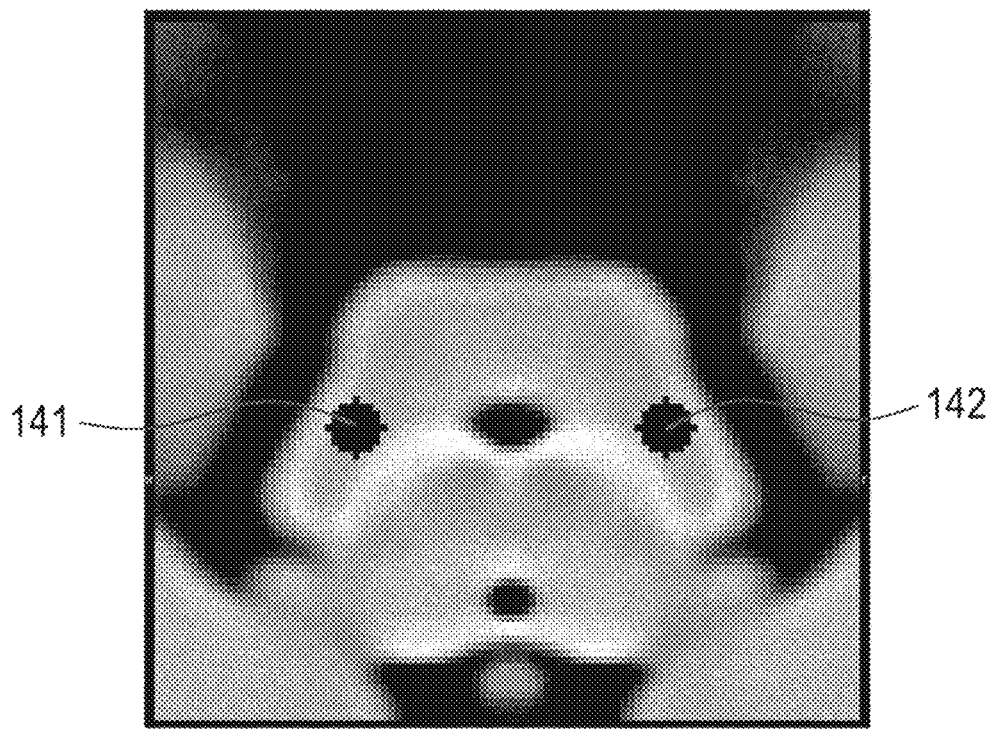
FIG. 7 illustrates an example of segmenting and calculating a reference region, according to the present disclosure.

FIG. 7 illustrates an example of segmenting and calculating a reference region, according to the present disclosure.

Referring to FIG. 7, as the reference region Red, a first reference region 141 and a second reference region 142 are illustrated.

Further, the CR image generating unit 150 provides a function of generating a CR image in which the contrast ratio (CR) value is mapped to each voxel of the image based on the spatially normalized image.

Figure 8:
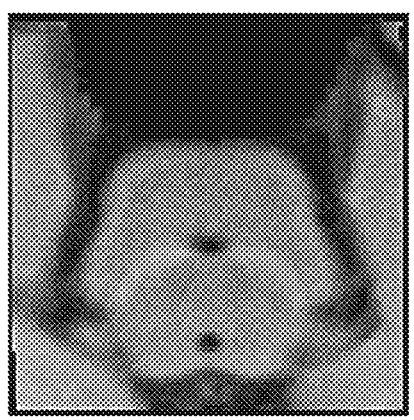
FIG. 8 illustrates an example of a CR image generated by mapping a contrast ratio (CR) value to each voxel, according to the present disclosure.
Figure 8:
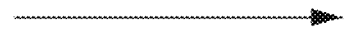
Figure 8:
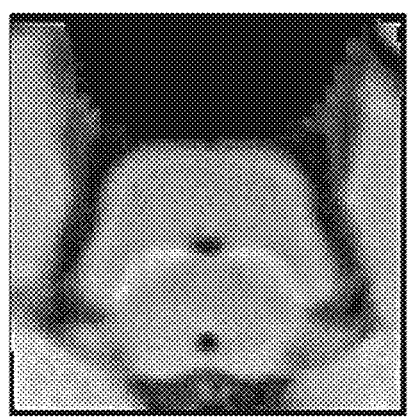

FIG. 8 illustrates an example of a CR image generated by mapping a contrast ratio (CR) value to each voxel, according to the present disclosure.

In the meantime, the CR image generating unit 150 may calculate a contrast ratio value using a mean value calculated by the reference region segmenting and calculating unit 140.

The contrast ratio value may be calculated by the following Equation 1.

$$CR_v = \frac{(SI_v - \text{mean}SI_{Ref})}{\text{mean}SI_{Ref}} \quad \text{[Equation 1]}$$

In Equation 1, $CR_v$ is the contrast ratio value, $SI_v$ is a signal intensity of each voxel, and $\text{mean}SI_{Ref}$ refers to the mean value.

Further, the CR calculating unit 160 provides a function of segmenting a predetermined vulnerable region based on the generated CR image and calculating a mean CR in the segmented vulnerable region.

Here, the predetermined vulnerable region may be a region which significantly differs by more than a predetermined reference when a neuromelanin region of the normal group and a neuromelanin region of a patient group are compared.

Representatively, the predetermined vulnerable region may include a nigrosome1 region and a nigrosome2 region.

Figure 9A:
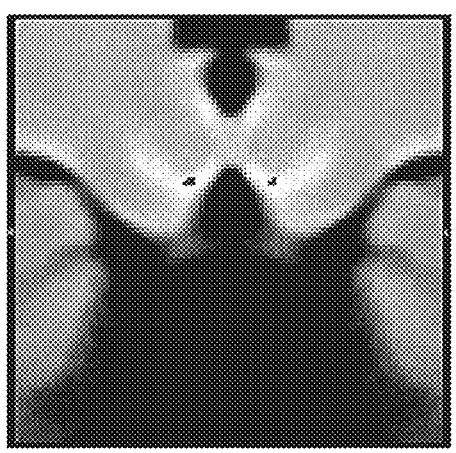
FIGS. 9A and 9B illustrate an example of segmenting a vulnerable region and calculating a mean CR, based on a contrast ratio (CR) image generated in FIG. 8.
Figure 9A:
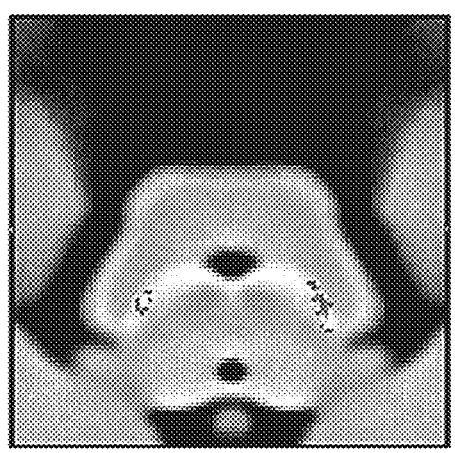
Figure 9A:
Figure 9B:
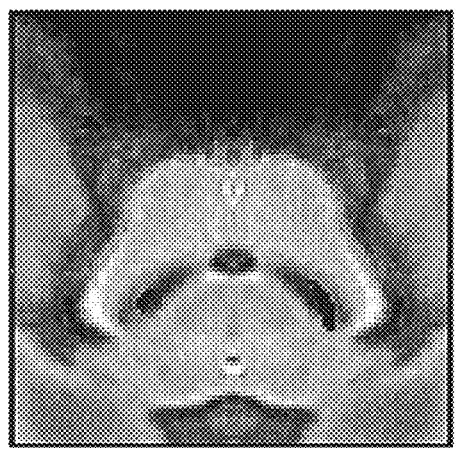
Figure 9B:
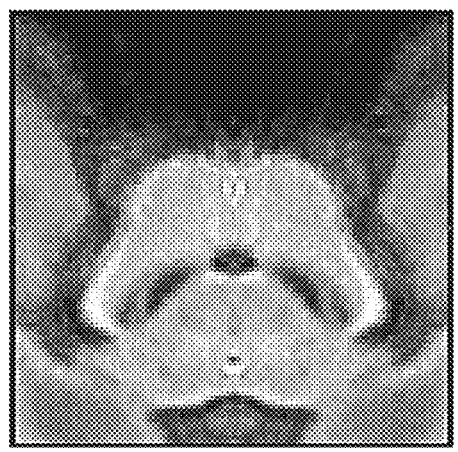
Figure 9B:
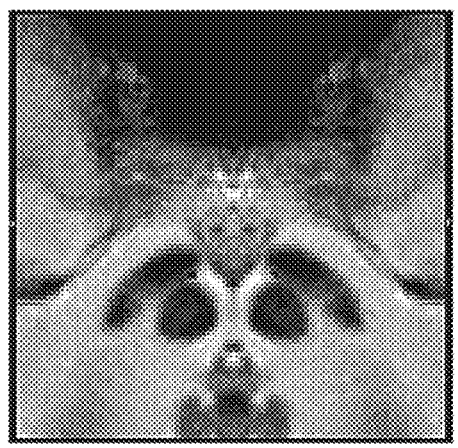
Figure 9B:
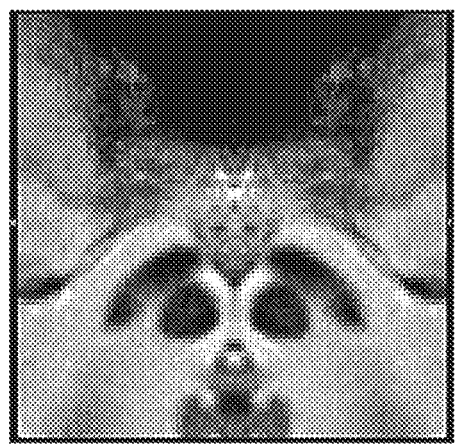

FIGS. 9A and 9B illustrate an example of segmenting a vulnerable region and calculating a mean CR, based on a contrast ratio (CR) image generated in FIG. 8.

The vulnerable region is a region which statistically significantly differs in the neuromelanin regions of the normal group and the patient group and FIGS. 9A (a) and (b) and FIGS. 9B (a) to (d) illustrate regions (50 normal people and 50 IPDs) which statistically significantly differ in the neuromelanin region.

When the regions of FIGS. 9A (a) and (b) and FIGS. 9B (a) to (d) are overlaid with susceptibility map weighted imaging (SMWI) templates, the regions may correspond to the nigrosome1 and nigrosome2 regions.

Here, nigrosome1 and nigrosome2 are areas which are affected in early Parkinson's diseases.

Further, the mean CR of the vulnerable region may be calculated by combination of the nigrosome1 and 2 regions or left and right areas.

The mean CR calculated herein may be utilized in the image analyzing unit 40.

In the meantime, according to another exemplary embodiment of the present disclosure, a method which generates and utilizes a within-subject template for a longitudinal study may be proposed.

Figure 10:
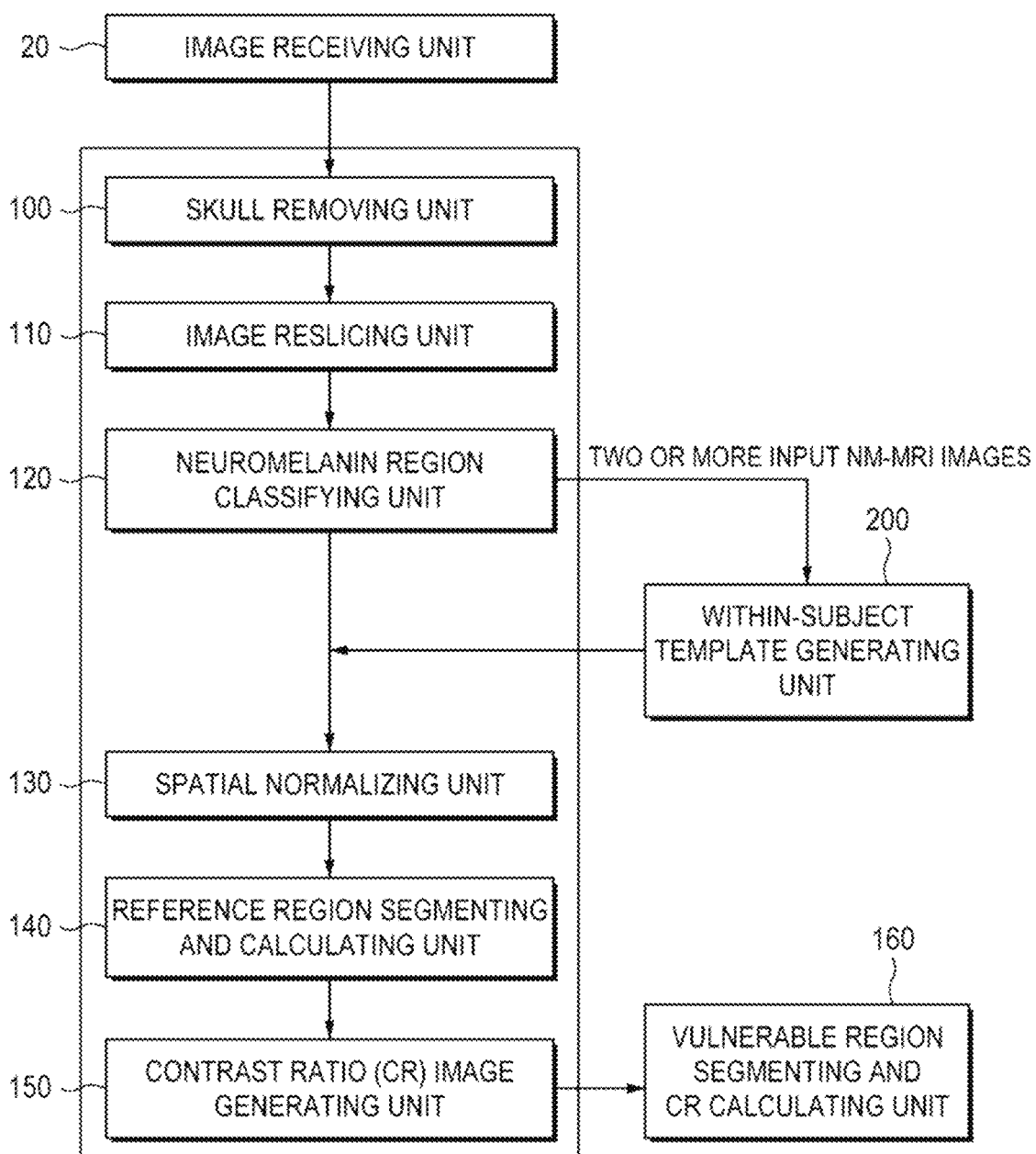
FIGS. 10 and 11 illustrate an example of generating and using a within-subject template when a plurality of neuromelanin MRI images is input, according to the present disclosure.
Figure 11:
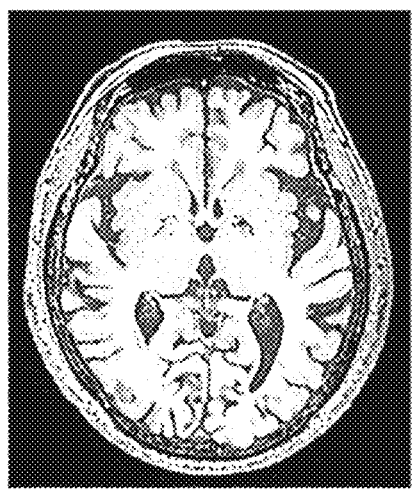
Figure 11:
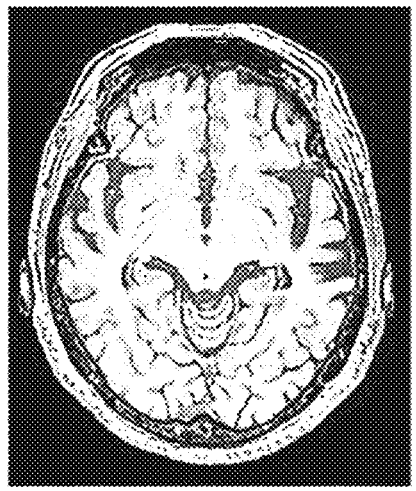
Figure 11:

FIGS. 10 and 11 illustrate an example of generating and using a within-subject template when a plurality of neuromelanin MRI images is input, according to the present disclosure.

Referring to FIG. 10, when a plurality of MRI images is input with respect to the same subject, a template generating unit 200 which generates a within-subject template using neuromelanin region data included in the plurality of MRI images may be further included.

At this time, the spatial normalizing unit 130 performs the spatial normalization using the within-subject template and the within-subject template may be used for the longitudinal study for the same subject.

As described above, during the longitudinal study, when the within-subject template generating process is added, the within-subject template as illustrated in FIG. 11 (c) may be generated using input NM-MRI images (two or more) as illustrated in FIGS. 11 (a) and (b).

In order to observe variance of data for the same person captured at different timings, the within-subject template is generated and the within-subject template may minimize the variability of the images captured at different timings according to the elapse of time.

That is, the within-subject template may be considered as an image (template) averaged over time.

Configuration and Operation of Image Processing Unit

The image processing unit 30 provides a function of segmenting a neuromelanin region classifying area and calculating a volume.

Figure 12:
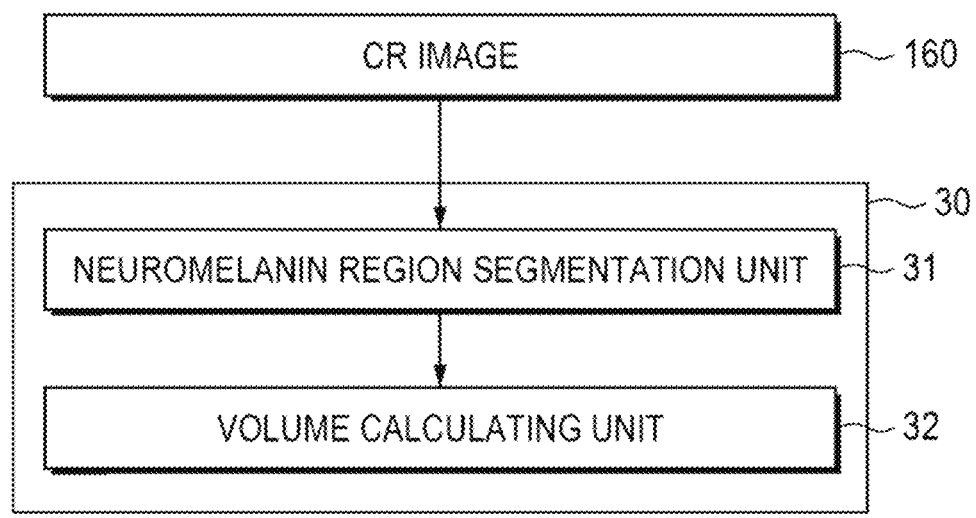
FIG. 12 is a view for explaining a configuration of an image processing unit which segments a neuromelanin region and calculates a volume, according to the present disclosure.

FIG. 12 is a view for explaining a configuration of an image processing unit which segments a neuromelanin region and calculates a volume, according to the present disclosure.

Referring to FIG. 12, the image processing unit 30 includes a segmentation unit 31 which analyzes the preprocessed MRI image and classifies a first image including the neuromelanin region and a volume calculating unit 32 which detects the neuromelanin region from the classified first image and calculates a volume of the neuromelanin region.

The volume calculating unit 32 may calculate the volume of the neuromelanin region using a number of voxels related to the first image and a voxel size.

In the meantime, as a method for analyzing the preprocessed MRI image to classify the first image including the neuromelanin region by the segmentation unit 31, one of three methods as follows may be used:
(1) A method using graph-cut
(2) A method using deep learning
(3) A method using specific thresholding First, the segmentation unit 31 may classify the first image based on a graph-cut algorithm which uses a foreground image configured by voxels having a high probability of including a neuromelanin region and a background image generated based on the foreground image.

Figure 13:
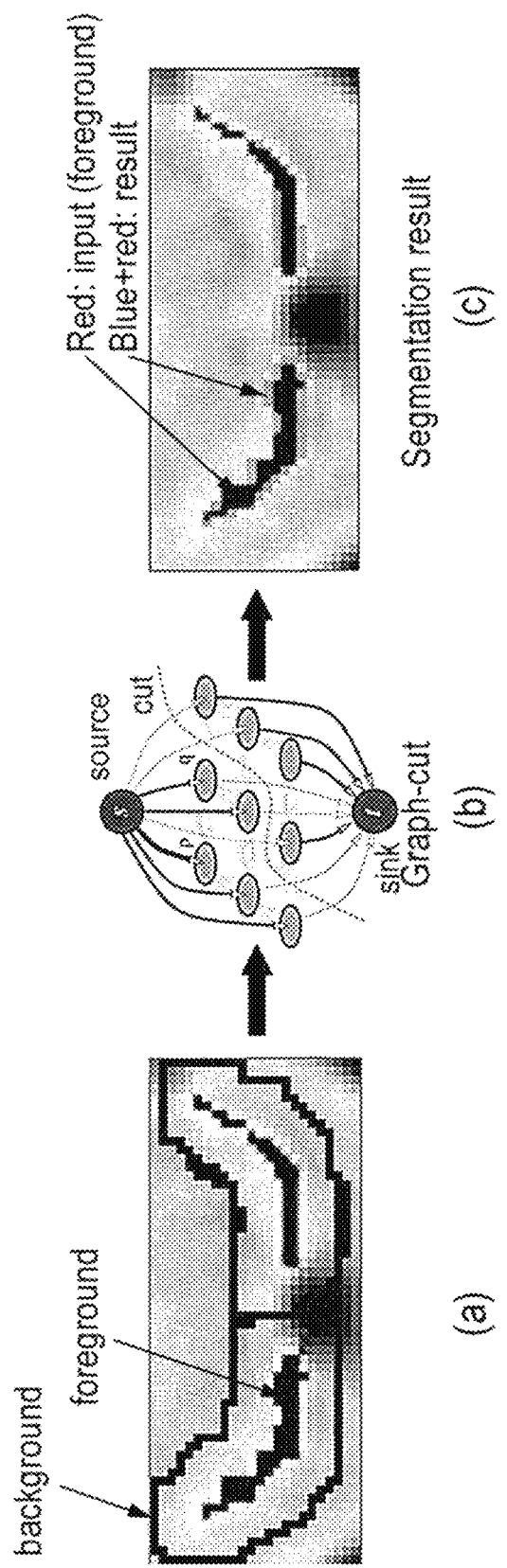
FIG. 13 is a view for explaining a method using a graph-cut, with regard to the operation of the image processing unit according to the present disclosure.

FIG. 13 is a view for explaining a method using a graph-cut, with regard to the operation of the image processing unit according to the present disclosure.

Referring to FIGS. 13 (a) to (c), as a method for segmenting the neuromelanin region classifying area using the graph-cut algorithm, an example of segmentation using a foreground image and a background image is illustrated.

Here, the foreground image is an image configured by voxels having a high probability of being a neuromelanin region and the background image is an image generated based on the foreground image.

Next, the segmentation unit 31 may classify the first image based on a deep neural network trained with data in which a brain image and a neuromelanin region area are labeled, with regard to the method using deep learning.

Figure 14:
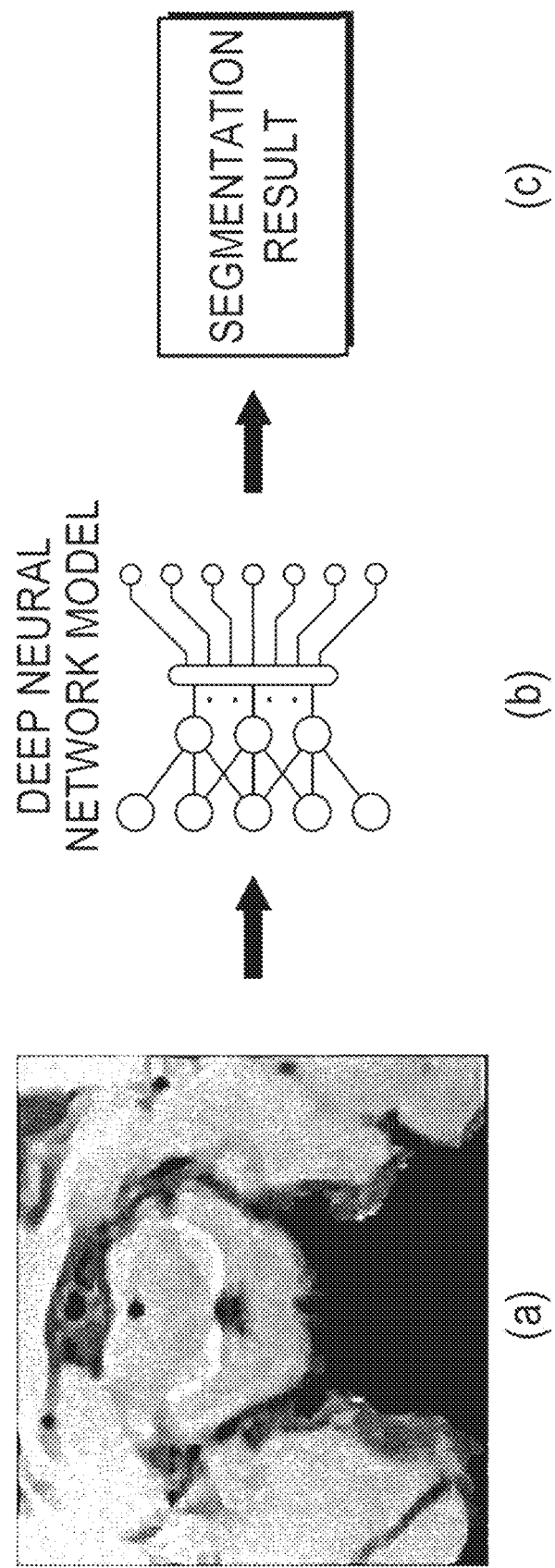
FIG. 14 is a view for explaining a method using deep learning, with regard to the operation of the image processing unit according to the present disclosure.

FIG. 14 is a view for explaining a method using deep learning, with regard to the operation of the image processing unit according to the present disclosure.

Referring to FIGS. 14 (a) to (c), an example of segmenting the neuromelanin region using a deep neural network module trained with data in which the brain image and the neuromelanin region are labeled is illustrated.

Finally, the segmentation unit 31 may extract a factor which is equal to or higher than a predetermined signal intensity and classify the first image using the extracted factor, with regard to the method using specific thresholding.

According to this method, only the signal intensities which are higher than a threshold are used for segmentation and the threshold value may be calculated as follows.

As a process of calculating a neuromelanin volume using a threshold value, a process of selecting an optimized calibration factor to calculate a signal intensity and a contrast variation may be necessary.

Further, the specific calibration factor may increase the SD value by 0.25 and another threshold may be calculated by the following Equation 2.

$$SI_{thre} = SI_{BGmean} + (Cal_{opt} \times SD_{BG}) \quad \text{[Equation 2]}$$

As a result, based on the above Equation 2, the segmentation is performed by remaining values which are higher than the threshold to perform the segmentation of the neuromelanin region.

Configuration and Operation of Image Analyzing Unit and Diagnostic Information Output Unit As described above, the image processing unit 30 may calculate a volume of the neuromelanin region based on the first region and according to the exemplary embodiment of the present disclosure, a clinical information receiving unit 60 which acquires clinical information may be further utilized.

At this time, the image analyzing unit 40 may calculate a neuromelanin atrophy degree using the calculated volume of the neuromelanin region and the acquired clinical information together.

Further, the image analyzing unit 40 may diagnose whether the patient has the Parkinson's disease based on the calculated neuromelanin atrophy degree.

Here, the neuromelanin atrophy degree may be calculated by comparing a volume of the neuromelanin region extracted from an image of a normal group and a volume of the neuromelanin region of the patient.

Further, the image analyzing unit 40 may convert the calculated neuromelanin atrophy degree into percentile information according to ages.

Further, the image analyzing unit 40 may calculate a neuromelanin atrophy rate of the patient using a plurality of neuromelanin atrophy degrees acquired at a predetermined period.

Thereafter, the neuromelanin atrophy rate of the patient deducted by the image analyzing unit 40 may be displayed and provided in various forms by means of the diagnostic information output unit 50.

Figure 15:
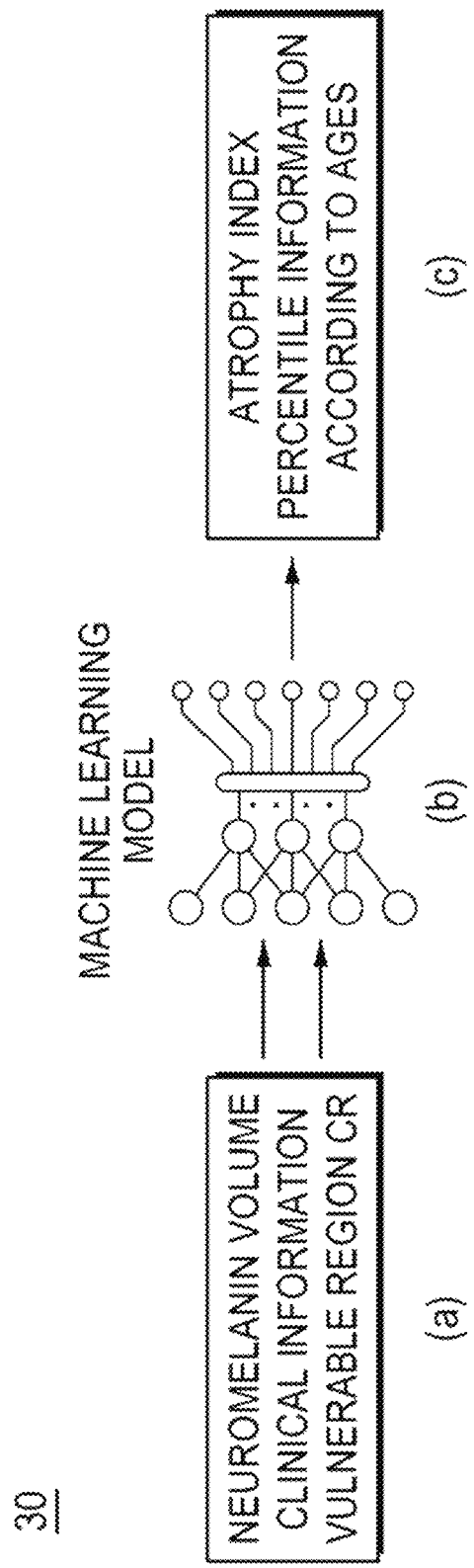
FIG. 15 illustrates an example of acquiring neuromelanin atrophy degree information according to ages, using the neuromelanin volume and clinical information, by an image analyzing unit of the present disclosure.

FIG. 15 illustrates an example of acquiring neuromelanin atrophy degree information according to ages, using the neuromelanin volume and clinical information, by an image analyzing unit of the present disclosure.

Referring to FIGS. 15 (a) to (c), the image analyzing unit 40 calculates a neuromelanin atrophy degree using the calculated volume of the neuromelanin region and the acquired clinical information, diagnoses whether the patient has the Parkinson's disease based on the calculated neuromelanin atrophy degree, and may convert the calculated neuromelanin atrophy degree into percentile information according to ages.

Specifically, the image analyzing unit 40 may acquire the neuromelanin atrophy degree according to ages using the neuromelanin volume and the clinical information. The atrophy index refers to a value obtained by converting the individual's input neuromelanin volume based on a standard score calculated by the neuromelanin volume extracted from the image of a normal group according to ages.

The following Equation 3 is an equation which basically acquires a standard score including z-score and t-score.

$$z - \text{score}_{ind} = \frac{(v_{ind} - \mu_{NC})}{\sigma_{NC}} \quad \text{[Equation 3]}$$

In Equation 3, $v_{ind}$ is an individual's extracted neuromelanin volume, $\mu_{NC}$ is a mean neuromelanin volume of an NC population, and $\sigma_{NC}$ is a standard deviation of a neuromelanin volume of an NC population.

The standard score may be calculated in various methods according to the input clinical information.

Representatively, the following Equation 4 proposes a method of calculating a standard score (W-score) in which age is corrected.

$$w - \text{score}_{ind} = \frac{v_{ind} - X}{\sigma_{NC}} \quad \text{[Equation 4]}$$

In Equation 4, $v_{ind}$ is an individual's extracted neuromelanin volume, X is an expected value in which age is corrected, and $\sigma_{NC}$ is a standard deviation of a neuromelanin volume of an NC population.

A machine learning model which is applicable to the present disclosure may be a module in which a neuromelanin volume and clinical information of the normal person and an atrophy degree are learned.

Further, according to the present disclosure, when the individual's neuromelanin volume and clinical information are input, an atrophy index for individual and age may be output and this atrophy index may be converted into percentile information according to ages to be output.

FIG. 16 illustrates an example of visibly displaying percentile information according to ages, by a diagnostic information output unit, according to the present disclosure.

Referring to FIG. 16, a 52-year-old male has an atrophy degree of 0.83 and 72 percentile and thus a personalized management and treatment may be correspondingly performed.

Further, according to the present disclosure, the longitudinal study may be performed by periodic diagnosis.

The longitudinal study may be performed by calculating an atrophy rate using NM-MRIs captured for the same person with a predetermined period.

Here, the atrophy rate refers to a changed degree of a neuromelanin volume as baseline data and a neuromelanin volume as follow-up data and may be provided through the diagnostic information output unit 50 in various forms.

For example, information saying that "a neuromelanin volume of 65-year-old male is reduced by approximately 8.5% for 1.31 years" may be provided.

As another example, information saying that "a neuromelanin volume of 63-year-old female is reduced by approximately 2 ml for 1.23 years" may be provided.

Parkinson's Disease Diagnosing Method

A method for diagnosing the Parkinson's disease will be explained based on the above-described configuration of the present disclosure.

First, a step S10 of acquiring an MRI image acquired by capturing a brain of a patient by the image receiving unit 20 is performed.

At this time, the image receiving unit 20 may additionally acquire a PET image related to the brain of the patient as well as the MRI.

Next, the image preprocessing unit 25 performs a step S20 of preprocessing the acquired MRI image to observe a neuromelanin region which is used as an image bio marker of the Parkinson's disease.

Here, as the most important function of the image preprocessing unit 25, the image preprocessing unit 25 may generate a contrast ratio (CR) image based on the acquired MRI image.

Further, the image processing unit 30 analyzes the preprocessed MRI image to classify a first image including the neuromelanin region (S30).

Next, the image processing unit 30 performs an operation of detecting the neuromelanin region from the classified first image (S40).

The image processing unit 30 may calculate a volume of the neuromelanin region based on the first image and the image analyzing unit 40 diagnoses the Parkinson's disease of the patient based on the calculated volume of the neuromelanin region.

The image processing unit 30 may calculate the volume of the neuromelanin region using a number of voxels related to the first image and a voxel size.

After the step S40, the image analyzing unit 40 may analyze whether the detected neuromelanin region is normal to diagnose whether the patient has the Parkinson's disease (S50).

In the step S50, the image analyzing unit 40 calculates a neuromelanin atrophy degree using the calculated volume of the neuromelanin region and the acquired clinical information together and may diagnose whether the patient has the Parkinson's disease based on the calculated neuromelanin atrophy degree.

Further, the image analyzing unit 40 may convert the calculated neuromelanin atrophy degree into percentile information according to ages.

Next, the image analyzing unit 40 may calculate a neuromelanin atrophy rate of the patient using a plurality of neuromelanin atrophy degrees acquired at a predetermined period (S60) and the diagnostic information output unit 50 may provide a function of displaying the neuromelanin atrophy rate of the patient in various forms (S70).

Method of Increasing Probability of Successful Clinical Trial by Utilizing Parkinson's Disease Diagnosing Method Using Artificial Intelligence to Screen Patient Group and Normal Group The Parkinson's disease diagnosing method and apparatus according to the present disclosure as described above is utilized to screen the patient group and the normal group to increase a probability of successful clinical trials.

That is, the present disclosure may provide a device, a system, and a method of utilizing the Parkinson's disease diagnosing method using artificial intelligence to screen a patient group and a normal group to increase the probability of successful clinical trials.

A result of clinical trials for demonstration of drug efficacy is determined by showing a statistical significance indicating whether to achieve a predicted expected effect for clinical trial participants. However, when the Parkinson's disease diagnosing method and apparatus according to the present disclosure are applied, only Parkinson's disease patients exactly targeted by new drugs are included as clinical trial subjects so that the probability of successful clinical trials may be increased as much as possible.

First, problems of existing new drug clinical trials will be described in advance.

A result of clinical trials for demonstration of drug efficacy is determined by showing a statistical significance indicating whether to achieve a predicted expected effect for clinical trial participants.

In the meantime, in the case of the Parkinson's disease, it is inevitable to rely on UPDRS evaluation, neurological examination, and Hoehn & Yarr stage evaluation (0 to 5 stages) to measure whether symptoms are improved by the drug efficacy. However, these methods are based on questionnaire and have problems in that the scale of data is not detailed.

Therefore, in order to prove the statistical significance, a numerical value of an evaluation scale needs to be statistically significantly increased before and after medication or as compared to a placebo group. The higher the predicted increase value, the smaller the number of target subjects and the higher the probability of achieving statistical significance.

In this case, if the predicted increase value is small, the number of target subjects increases as well and the difficulty of statistical proof is increased.

As a result, it is very difficult to increase one step of evaluation scale of the Parkinson's disease, so that there is a problem in that a possibility of passing the clinical trial is very low.

In the present disclosure, in order to solve the above-described problem, only Parkinson's disease patients exactly targeted by the new drug are included as subjects of the clinical trials to increase a probability of successful clinical trials as much as possible.

One of important failure factors in a new drug development process for central nervous system drugs is the difficulty of screening the correct subjects and screening a drug response group.

Since a response rate to the placebo for the central nervous system drugs is particularly high, an important strategy of increasing the success rate is to reduce the heterogeneity of the subject group and setting a biomarker capable of predicting a drug reactivity.

Further, since it takes a long time to confirm the Parkinson's disease (approximately three months), a screening test is difficult so that there is a problem in that it is very difficult to include only the Parkinson's disease patients targeted by new drugs as subjects of clinical trials.

Therefore, the Parkinson's disease diagnosing method using artificial intelligence according to the present disclosure may be utilized to screen a patient group and a normal group to increase the probability of successful clinical trials.

According to the exemplary embodiment of the present disclosure, first, a step S100 of recruiting an experiment candidate group for a clinical trial to demonstrate a drug efficacy is performed.

Next, a step S110 of acquiring an image with respect to a plurality of experimental candidate groups, a step S120 of preprocessing the acquired MRI image to observe the neuromelanin region used as an image bio marker of the Parkinson's disease, a step S130 of analyzing the preprocessed MRI image to classify the first image including the neuromelanin region, a step S140 of detecting the neuromelanin region from the classified first image, and a step S150 of analyzing whether the detected neuromelanin region is normal to diagnose whether the patient has the Parkinson's disease are performed.

The steps S110 to S150 correspond to the above-described steps S10 to S50, respectively so that redundant description will be omitted to clarify the specification.

Next, when a diagnosis result is derived through the step S150, a step S160 of classifying the plurality of experimental candidate groups into an actual Parkinson's disease patient group and a normal patient group based on the diagnosis result may be performed.

In this case, a step S170 of performing a clinical trial and a step S180 of demonstrating a drug efficacy based on a clinical trial result are performed only on the subject classified as the actual Parkinson's disease patient group. Therefore, only the Parkinson's disease patients exactly targeted by the new drug are included as clinical trial subjects so that the probability of successful clinical trial may be increased.

As a result, the Parkinson's disease diagnosing method using artificial intelligence according to the present disclosure may be utilized to screen a patient group and a normal group to increase the probability of successful clinical trials.

The above-described steps S100 to S180 may be performed independently by the Parkinson's disease information providing apparatus 1 or may be applied to perform the overall operation together with the Parkinson's disease information providing apparatus 1 by providing a separate server or a separate central management device.

More, in the above description, even though a method for increasing the efficiency of the new drug development based on the Parkinson's disease has been described, a new drug efficacy may also be demonstrated by dividing stages which represent the severity of the Parkinson's disease.

For example, the statuses of the plurality of patients are divided into N stages based on the technology proposed by the present disclosure, and only patient groups corresponding to each stage are selected to perform the clinical trials. Therefore, the new drug efficacy and the probability of successful clinical trials in precise stages may be increased.

Effect According to Present Disclosure

As described above, according to the Parkinson's disease information providing apparatus and method according to the present disclosure, only images including the neuromelanin region are classified from the MRI and the neuromelanin region is analyzed from the classified image to diagnose the Parkinson's disease.

Further, according to the present disclosure, the Parkinson's disease is diagnosed using the image so that the Parkinson's disease is precisely diagnosed using the MRI equipment, which is generally supplied, and the precision of the diagnosis result is improved.

Further, according to the present disclosure, only the neuromelanin region may be observed.

Specifically, the acquired MRI image is preprocessed to observe the neuromelanin image, the preprocessed MRI image is analyzed to classify an image including the neuromelanin image, the neuromelanin image is detected from the classified image, and whether the detected neuromelanin region is normal is analyzed to diagnose whether the patient has the Parkinson's disease.

Further, according to the present disclosure, the neuromelanin region may be effectively detected by machine learning.

Specifically, according to the present disclosure, the Parkinson's disease may be diagnosed by performing at least one operation of angle adjustment, image enlargement, and reslice based on an image from which a skull region is removed, detecting a region including neuromelanin using a deep neural network model, performing spatial normalization using a template image, and generating a CR image in which a contrast ratio (CR) value is mapped to each voxel of the image to diagnose the Parkinson's disease.

Further, according to the present disclosure, it is possible to provide an apparatus and a method which segment a predetermined vulnerable region based on a generated CR image and calculate a mean CR in the segmented vulnerable region to perform preprocessing on the image.

Further, according to the present disclosure, it is possible to provide a longitudinal study function by generating a within-subject template and performing spatial normalization using neuromelanin region data included in a plurality of MRI images when there is a plurality of MRI images input with respect to the same object.

Further, according to the present disclosure, it is possible to calculate a volume of a neuromelanin region of a patient, calculate a neuromelanin atrophy degree using the calculated volume of the neuromelanin region and the acquired clinical information together, and diagnose whether the patient has the Parkinson's disease based on the calculated neuromelanin atrophy degree.

Further, according to the present disclosure, the neuromelanin atrophy rate of the patient is calculated using a plurality of neuromelanin atrophy degrees acquired at a predetermined period and the neuromelanin atrophy rate of the patient is displayed and provided in various forms.

In addition, according to the present disclosure, a result of clinical trials for demonstration of drug efficacy is determined by showing a statistical significance indicating whether to achieve a predicted expected effect for clinical trial participants. However, when the Parkinson's disease diagnosing method and apparatus according to the present disclosure are applied, only Parkinson's disease patients exactly targeted by new drugs are included as clinical trial subjects so that the probability of successful clinical trials may be increased as much as possible.

That is, the Parkinson's disease diagnosing method using artificial intelligence according to the present disclosure may be utilized to screen a patient group and a normal group to increase the probability of successful clinical trials.

In the meantime, a technical object to be achieved in the present disclosure is not limited to the aforementioned effects, and another not-mentioned effects will be obviously understood by those skilled in the art from the description below.

The above-described exemplary embodiments of the present disclosure may be implemented through various methods. For example, the exemplary embodiments of the present disclosure may be implemented by a hardware, a firmware, a software, or a combination thereof.

When the exemplary embodiment is implemented by the hardware, the method according to the exemplary embodiment of the present disclosure may be implemented by one or more application specific integrated circuits (ASICs), digital signal processors (DSPs), digital signal processing devices (DSPDs), programmable logic devices (PLDs), field programmable gate arrays (FPGAs), a processor, a controller, a microcontroller, or a microprocessor.

When the exemplary embodiment is implemented by the firmware or the software, the method according to the exemplary embodiment of the present disclosure may be implemented by a module, a procedure, or a function which performs a function or operations described above. The software code is stored in the memory unit to be driven by the processor. The memory unit is located inside or outside the processor and may exchange data with the processor, by various known units.

As described above, the detailed description of the exemplary embodiments of the disclosed present disclosure is provided such that those skilled in the art implement and carry out the present disclosure. While the disclosure has been described with reference to the preferred embodiments, it will be understood by those skilled in the art that various changes and modifications of the present disclosure may be made without departing from the spirit and scope of the disclosure. For example, those skilled in the art may use configurations disclosed in the above-described exemplary embodiments by combining them with each other. Therefore, the present disclosure is not intended to be limited to the above-described exemplary embodiments but to assign the widest scope consistent with disclosed principles and novel features.

The present disclosure may be implemented in another specific form within the scope without departing from the spirit and essential feature of the present disclosure. Therefore, the detailed description should not restrictively be analyzed in all aspects and should be exemplarily considered. The scope of the present disclosure should be determined by rational interpretation of the appended claims and all changes are included in the scope of the present disclosure within the equivalent scope of the present disclosure. The present disclosure is not intended to be limited to the above-described exemplary embodiments but to assign the widest scope consistent with disclosed principles and novel features. Further, claims having no clear quoting relation in the claims are combined to configure the embodiment or may be included as new claims by correction after application.

What is claimed is:

1. A Parkinson's disease information providing apparatus using a neuromelanin image, comprising:
   an image receiving unit which acquires a magnetic resonance imaging (MRI) image obtained by capturing a brain of a patient;
   an image preprocessing unit which preprocesses the acquired MRI image to observe a neuromelanin region used as an image bio marker of the Parkinson's disease;
   an image processing unit which analyzes the preprocessed MRI image to classify a first image including the neuromelanin region and detects the neuromelanin region from the classified first image; and
   an image analyzing unit which analyzes the detected neuromelanin region to determine information of the patient related to the Parkinson's disease,
   wherein the image processing unit calculates a volume of the neuromelanin region based on the first image, and the image analyzing unit determines information of the patient related to the Parkinson's disease using the calculated volume of the neuromelanin region.

2. The Parkinson's disease information providing apparatus according to claim 1, wherein the image preprocessing unit generates a contrast ratio (CR) image based on the acquired MRI image.

3. The Parkinson's disease information providing apparatus according to claim 2, wherein the image preprocessing unit includes:
   a skull removing unit which removes a skull region from the acquired MRI image;
   an image reslicing unit which performs at least one operation of angle adjustment, image enlargement, and reslice, based on the image in which the skull region is removed;
   a neuromelanin region classifying unit which detects a first region including the neuromelanin using a deep neural network model, based on the image transmitted from the image reslicing unit;
   a spatial normalizing unit which performs the spatial normalization using a template image based on an image in which the first region is detected;
   a CR image generating unit which generates a CR image in which the contrast ratio (CR) value is mapped to each voxel of the image, based on the spatially normalized image; and
   a calculating unit which segments a predetermined vulnerable region and calculates a mean CR in the segmented vulnerable region, based on the generated CR image.

4. The Parkinson's disease information providing apparatus according to claim 3, wherein the neuromelanin region classifying unit displays a boundary of the first region to be identified and crops an image of the first region.

5. The Parkinson's disease information providing apparatus according to claim 3, wherein the spatial normalizing unit performs the spatial normalization using at least one of a first template image generated from a neuromelanin MRI image of a normal person and a second template image generated from an anatomical image based on a T1-weighted MRI.

6. The Parkinson's disease information providing apparatus according to claim 5, wherein the spatial normalizing unit performs the spatial normalization by matching the first template image after matching using the second template image.

7. The Parkinson's disease information providing apparatus according to claim 3, further comprising:
   a reference region segmentation unit which segments a reference region based on an Atlas-based segmentation method using atlas which is a reference image defined on a template space, based on the spatially normalized image and calculates a mean value in the segmented reference region,
   wherein the CR image generating unit calculates the contrast ratio value using the calculated mean value.

8. The Parkinson's disease information providing apparatus according to claim 7, wherein the contrast ratio value is calculated by the following Equation 1, $$CR_v = \frac{(SI_v - \text{mean}SI_{Ref})}{\text{mean}SI_{Ref}} \qquad \text{[Equation 1]}$$

in Equation 1, $CR_v$ is the contrast ratio value, $SI_v$ is a signal intensity of each voxel, and $\text{mean}SI_{Ref}$ refers to the mean value.

9. The Parkinson's disease information providing apparatus according to claim 7, wherein the segmented reference region is a cerebral peduncles region.

10. The Parkinson's disease information providing apparatus according to claim 3, wherein the predetermined vulnerable region is a region which significantly differs by a predetermined reference or more when a neuromelanin region of a normal group and a neuromelanin region of a patient group are compared.

11. The Parkinson's disease information providing apparatus according to claim 10, wherein the predetermined vulnerable region includes a nigrosome 1 region and a nigrosome 2 region.

12. The Parkinson's disease information providing apparatus according to claim 3, further comprising:
    when a plurality of MRI images is acquired with respect to the same subject,
    a template generating unit which generates a within-subject template which is an image averaged according to elapse of time using the neuromelanin region data included in the plurality of MRI images,
    wherein the spatial normalizing unit performs the spatial normalization using the within-subject template and the within-subject template is used for a longitudinal study for the same subject.

13. The Parkinson's disease information providing apparatus according to claim 1, wherein the image processing unit calculates the volume of the neuromelanin region using a number of voxels related to the first image and a voxel size.

14. The Parkinson's disease information providing apparatus according to claim 1, wherein the image processing unit classifies the first image based on a graph-cut algorithm which uses a foreground image configured by voxels having a high probability of including the neuromelanin region and a background image generated based on the foreground image.

15. The Parkinson's disease information providing apparatus according to claim 1, wherein the image processing unit classifies the first image based on a deep neural network trained with data in which a brain image and a neuromelanin region image are labeled.

16. The Parkinson's disease information providing apparatus according to claim 1, wherein the image processing unit extracts a factor which is equal to or higher than a predetermined signal intensity and classifies the first image using the extracted factor.

17. The Parkinson's disease information providing apparatus according to claim 1, wherein the image processing unit calculates a volume of the neuromelanin region based on the first image and further includes: a clinical information receiving unit which acquires clinical information, and the image analyzing unit calculates a neuromelanin atrophy degree using the calculated volume of the neuromelanin region and the acquired clinical information together and determines information of the patient related to the Parkinson's disease based on the calculated neuromelanin atrophy degree.

18. The Parkinson's disease information providing apparatus according to claim 17, wherein the neuromelanin atrophy degree is calculated by comparing a volume of the neuromelanin region extracted from an image of a normal group and a volume of the neuromelanin region of the patient.

19. The Parkinson's disease information providing apparatus according to claim 17, wherein the image analyzing unit converts the calculated neuromelanin atrophy degree into percentile information according to ages.

20. The Parkinson's disease information providing apparatus according to claim 17, wherein the image analyzing unit calculates a neuromelanin atrophy rate of the patient using a plurality of neuromelanin atrophy degrees acquired at a predetermined period and further includes a diagnostic information output unit which displays the neuromelanin atrophy rate of the patient.

21. A system which increases a probability of successful clinical trials by screening a patient group having the Parkinson's disease using a Parkinson's disease information providing apparatus including an image receiving unit, an image preprocessing unit, an image processing unit, and an image analyzing unit, and a central management unit and/or a server which communicates with the Parkinson's disease information providing apparatus, wherein the image receiving unit acquires magnetic resonance imaging (MRI) images obtained by capturing brains of a plurality of patients which is a clinical trial experimental candidate group for demonstration of drug efficacy, the image preprocessing unit preprocesses the acquired MRI images to observe a neuromelanin region used as an image bio marker of the Parkinson's disease, the image processing unit analyzes the preprocessed MRI image to classify a first image including the neuromelanin region and detects the neuromelanin region from the classified first image, the image analyzing unit analyzes the detected neuromelanin region to determine information of the patient related to the Parkinson's disease and transmits at least one information about a first patient which satisfies a first condition, among the plurality of patients, to the central management unit and/or the server, based on the information of the patient, the central management unit and/or the server uses a clinical trial result for the first patient to demonstrate the drug efficacy, the image processing unit calculates a volume of the neuromelanin region based on the first image, and the image analyzing unit determines the information of the patient related to the Parkinson's disease using the calculated volume of the neuromelanin region.

* * * * *